(12) United States Patent
Rao et al.

(10) Patent No.: US 6,458,831 B1
(45) Date of Patent: Oct. 1, 2002

(54) USE OF TWO PLANT PHENOLS IN THE TREATMENT OF ARTERIOSCLEROSIS

(75) Inventors: Janaswamy M. Rao; Ashok K. Tiwari; Pullela V. Srinivas; Jhillu S. Yadav; Kondapuram V. Raghavan, all of Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/698,060

(22) Filed: Oct. 30, 2000

(51) Int. Cl.⁷ ............................................. A61K 31/365
(52) U.S. Cl. ........................................ 514/461; 514/473
(58) Field of Search ................................. 549/313, 323; 514/461, 473

(56) References Cited

FOREIGN PATENT DOCUMENTS

WO        WO 00/59946      * 10/2000

OTHER PUBLICATIONS

Belletire et al, J. Org. Chem., vol. 53, p. 4724–4729 (1988).*

MacCrae et al, Biochemistry, vol. 23, No. 6, p. 1207–1220 (1984).*

Chem. Abstracts, vol. 131:44060 (1999); Jpn. Kokai 11180869, Jul. 6, 1999.*

* cited by examiner

*Primary Examiner*—Bernard Dentz
(74) *Attorney, Agent, or Firm*—Birch Stewart Kolasch & Birch LLP

(57) ABSTRACT

This invention relates to the isolation of two compounds namely (−)- Matairesinol and (−)- Wikstromol. These together with or associated with therapeutically acceptable additives are useful as antioxidants and as free radical scavengers.

5 Claims, 3 Drawing Sheets

R=R₁=R₂=H OR OH, R₃=OMe (−)-MATAIRESINOL (−)-WIKSTROMOL

USE OF TWO PLANT PHENOLS IN THE TREATMENT OF ARTERIOSCLEROSIS

FIELD OF THE INVENTION

This invention relates to the isolation of two compounds namely (−)- Matairesinol (4,4$^1$-dihydroxy-3, 3$^1$-dimethoxylignan-9, 9$^1$-olide) and (−) wikstromol (4,4$^1$, 8-trihydroxy-3, 3$^1$-dimethoxyliganan-9, 9$^1$-olide) from the plant source Cedrus deodara in significant yields. This invention also identifies the use of the said compounds as an antioxidant or a free radical scavenger.

PRIOR ART

The compound (−)-Matairesinol and (−)-wikstromol as such do not find much commercial value. The structural formulae of (−)-Matairesinol and (−)-wikstromol are as shown in FIG. 1. Lignans are widely distributed in angiosperms and gymnosperms. The range of their structures and biological activities is broad. Literature indicates that Matairesinol exhibits CAMP phosphodiesterase inhibition activity, [W. Donald Macrae and G. H. Neil Towers, Biological activities of Lignans, Phytochemistry 23 (6), 1207–20 (1984)]. (−)-Wikstromol is found to be active against p-388 lymphocyte leukemia and anti-HIV activity (M. K. Kharmlach, R. Dhal and E. Brown, Premieres syntheses totales du (+)-wikstromol, de la (−)-Trachelogenine, De la (−)-Nortrachelogenine et des lignoides apparentes—Tetrahedran 48, 10115–10126 (1992)).

The wood of Cedrus deodar possesses diaphoretic, diuretic and carminative properties, and it is useful in treatment of fevers, piles and pulmonary and urinary disorders. The extract of the bark is astringent and useful for fevers, diarrhea and dysentery. The oleoresin of deodar and the dark-colored oil obtained from the wood are valued for their application for ulcers and skin diseases. [Ref: Wealth of India, Vol.II, P.108–10 (1950) (published by CSIR)].

A close look at literature suggests that the lignan, secoisolariciresinalldiglycoside (SDG) which has been reported to possess multitude of activities is isolated from [U.S. Pat. No. 5,846,944]. The natural lignans (−)-matairesinol reduce the binding of H-labeled 5α-dihydrotestosterone (DHT) to human sex hormone-binding globulin (SHBG). [Matthias Schottnerand Gerhard Spiteller (J. Nat. Prod. 1998, 61, 119–121)]. P. K. Agarwal and R. P. Rastogi (Phytochemistry Vol 21, No 6, pp 1459–1461, 1982) reported isolation of two lignans meso-secoisolariciresinol and cedrusinin from Cedrus deodara.

The isolation of matariesional in 0.10% yield and (+)-wikstromol in 0.124% yield is reported from Wikstroemia viridiflora (Wikstromol, a new lignan from Wikstroemia viridiflora—Sheela Tandon and R. P. Rastogi; Phytochemistry 1976, vol 15, pp 1789–1791).

The extraction of the lignans and other constituents namely (−)-nortrachelogenin, carinol and carissanol from Carissa edulis has been reported by Hans Achenbach, Reiner Waibel and Ivan Addae-Mensah, Ref. Phytochemistry, Vol. 22, No. 3, pp. 749–753, 1983.

There is a considerable amount of epidemiological evidence indicating an association between diet rich in fruits and vegetables and a decreased risk of cardiovascular disease and certain forms of cancer. It is generally assumed that the active principles contributing to these protective effects are nothing but antioxidant phytochemicals.

Recent research is directed to find out phytochemicals from plant sources in highlighting the role of polyphenolic compounds of plant materials as antioxidants, antimutagenic, anti inflammatory, antiatherosclerotic, antidiabetic, antihepatotoxic and antimicrobial agents. [Overview of flax lignans by Neil D. Westcott and Alister D. Muir, Crop Utilization Section, Saskatoon Research Centre, Agriculture and Agri-Food Canada, 107, Science Place, Saskatoon, SK S7N 0X2, Canada in Volume II—January 2000—inform]. Alcoholic extract of stem C. deodara was found to have anti-cancer activity. [Ref. Medicinal Plants of India (ICMR) Vol.I, 1976, pp. 214 and 215].

Medicinal importance of antioxidant active principles are acquiring importance because of the involvement of free radical mediated oxidative stress in age related diseases.

Free radicals are highly energized molecules that contain an unpaired electron. These are produced through normal biological and environmental processes involving oxygen and can trigger chain reactions that product more free radicals. Normally there is a balance between the amount of free radicals generated in the body and antioxidants to protect against them. However, natural antioxidants present in the body can cope up only with the optimal generation of free radicals and any additional burden of free radicals or lack of antioxidant protection can tip this balance and lead to oxidative stress.

There is a need for free radical scavengers or antioxidant principles isolated from natural resources for preparation of formulations useful in alleviating diseases. Hence, it becomes necessary to look for other lignans possessing related and important biological properties.

Accordingly, the applicants conducted a detailed study on principles from Cedrus deodara and this investigation led to the isolation of two active principles namely, Matairesinol and wikstromol. These compounds although hitherto isolated from Wikstromia spp. were in low yields. Cedrus deodara hence is a new source for these lignans and their presence in this taxon in significantly high yields makes this invention more important.

OBJECTS OF THE INVENTION

The main object of the invention relates to use of (−)-wikstromol and/or (−)-matairesinol as free radical scavengers or antioxidants:

Another object of the invention is to provide methods for the isolation of (−)-wikstromol and/or (−)-matairesinol from Cedrus deodara.

Still another object of the invention is to provide methods for the treatment of arteriosclerosis.

SUMMARY OF THE INVENTION

Accordingly, the invention provides novel compositions containing (−)-wikstromol and/or (−)-matairesinol and useful as free radical scavengers and antioxidants. The invention further provides methods for the isolation of (−)-wikstromol and/or (−)-matairesinol from Cedrus deodara as well as use of the compounds for the treatment of arteriosclerosis.

DETAILED DESCRIPTION

Accordingly, the invention provides a composition comprising an effective amount of (−)-wikstromol together with or associated with an additive and useful as an antioxidant.

In yet another embodiment the composition contains an effective amount of (−)-matairesinol together with additives and useful as an antioxidant.

In another embodiment the additive is selected in such a manner that they has no effect with the active principles of the composition such as nutrients etc., The additive is such that they enhance and do not retard the activity of the active ingredients i.e. (−)-wikstromol and/or (−)-matairesinol.

In another embodiment the additive is selected from nutrients such as carbohydrates, proteins, sugar and pharmaceutically acceptable carriers.

In another embodiment the ratio of (−)-wikstromol and/or (−)-matairesinol with the additive is in the range between 0.1:10 to 2:10.

In an embodiment (−)-wikstromol and/or (−)-Matairesinol present in an amount of 250–300 mg.

Further the invention provides a process for the isolation of (−)-wikstromol and/or (−)-matairesinol from the *Cedrus deodara*, said process comprising the steps of a) extraction of the pulverized plant parts of *Cedrus deodara* with solvents to remove the essential oils;
b) concentrating the extract under vacuum to obtain a residue;
c) adding ethyl acetate to the residue obtained in step (b);
d) separating the solvents by conventional methods;
e) subjecting the residue to a first elution with about 3% methanol in chloroform to obtain (−)-matairesinol; and
f) subjecting the residue of step (e) to a second elution with about 5% methanol to obtain (−)-wikstromol.

The solvents used in step (a) are hexane and chloroform.

In another embodiment, the plant parts of *Cedrus deodara* such as bark and leaves are used for extraction.

In yet another embodiment, the wasted plant parts of *Cedrus deodara* are employed for isolation of the said compound. Preferably, the waste left after extraction of essential oil from the plant parts is used in the process.

There is enough literature, for example the article in Inform Vol. 11, pg. 118–121 that suggests that oxygen free radicals are responsible for development of arteriosclerosis. And, that, antioxidants are useful to retard hypercholestrolemic arteriosclerosis.

Accordingly, it is a further feature of the invention to treat arteriosclerosis wherein an effective amount of (−)-wikstromol or (−)-matairesinol is administered to a subject in need thereof.

(−)-wikstromol or (−)-matairesinol may be administered together with or in combination with therapeutically acceptable additives. The effective amount of (−)-wikstromol or (−)-matairesinol that may be administered to a subject can be readily determined by a person skilled in the art. However, it is recommended that the dosage of (−)-wikstromol or (−)-matairesinol administered may be in the range of 250 to 300 mg per dose, twice a day. While it is possible to administer the composition in oral as well as systemic routes, the oral route achieves the desired best results.

Compositions employing (−)-wikstromol or (−)-matairesinol may be prepared by conventional methods as known in the art. The compositions may be in the form of tablets, capsules or syrups, etc. Suitable additives as known in the art may be selected for the preparation of these compositions.

In essence the focus of the invention is to provide methods for using (−)-wikstromol and/or (−)-matairesinol for the preparation of compositions useful as a free radical scavenger and antioxidant.

The heartwood of *Cedrus deodara* finds extensive use in essential oil industry. The oil by name 'cedar wood' oil finds application in flavor and fragrances. The heartwood powder after extraction of essential oil is a by-product and waste. This invention relates to isolation and purification of the compounds (−)-matairesinol and (−)-wikstromol and use as antioxidants and for the treatment of arteriosclerosis.

This present invention relates to the isolation of two compounds namely (−)-Matairesinol and (4,4$^1$-dihydroxy-3, 3$^1$-dimethoxylignan-9, 9$^1$-olide) and (−)-wikstromol (4,4$^1$, 8-trihydroxy-3, 3$^1$-dimethoxyliganan-9, 9$^1$-olide) from a new source *Cedrus deodara*. This invention also relates to new use of the compounds as an antioxidant.

The present invention embodies isolation of (−)-Matairesinol and (−)-wikstromol, two antioxidant principles from an entirely new source and their free radical scavenging property compared with known biologically proved anti free radical agents, anti dyslipidemic and anti hepatotoxic efficacies.

BRIEF DESCRIPTION OF THE DRAWINGS

The invention is illustrated by the accompanying drawings wherein:

FIG. 1(*b*): represents (−)-wikstromol (4,4$^1$,8-trihydroxy-3, 3$^1$-dimethoxyliganan-9, 9$^1$-olide).

FIG. 1(*c*): represents (−)- Matairesinol (4,4$^1$-dihydroxy-3, 3$^1$-dimethoxylignan-9, 9$^1$-olide.

Some of the embodiments of the present invention are represented by the following examples, which should not be construed, as limitations on the inventive scope of the invention.

EXAMPLE 1

Experimental Protocol: a Process for the Isolation of (−)-Matairesinol and (−)- Wikstromol The dried wood powder of *Cedrus deodara* was loaded 200 g in a soxhlet apparatus. The powder was first extracted with hexane to remove the essential oil composition. The residue from the extraction of hexane was further extracted with chloroform. The chloroform extract was concentrated under vacuum. The thick syrupy residue was dissolved in ethyl acetate for about 50 g of residue around 60 ml of ethyl acetate. The isolation of residue in ethyl acetate was added drop wise to hexane 9 around 5 Lt. The solid separated 35-g was filtered off.

The solid was loaded on silica gel column 60 120 mesh, 3.5-cm dia. Column loaded to a height of 60 cm. Initially the column was eluted with chloroform followed by 3% methanol in chloroform of get (−)-Matairesinol.

Further elution of the column with 5% methanol in chloroform yielded (−)- Wikstromol.

The yield (−)-Matairesinol is around 0.06 g.

The yield (−) wikstromol is around 8.0 g.

The compounds (−)-Matairesinol and (−) wikstromol were obtained in 90% purity.

The spectrochemical and physical properties of (−) matairesinol and wikstromol are as under:

(−)-Matairesinol:

1. Molecular formula $C_{20}H_{22}O_6$
2. $^1$H-NMR: δ 2.53(4H, m), 2.95(2H, br s), 3.86(6H, s), 4.20–4.40(2H, m), 5.50(2H,—OH), 6.40–6.80(6H,m).
3. $^{13}$C-NMR: δ 34.48(C-8), 38.10(C-8), 40.90(C-7), 46.60(C-7), 46.60(C-7), 55.70(2×—OMe). 71.3(O-CH$_2$—O), 111.01, 111.53, 114.11, 114.40, 121.21, 121.95, 128.32, 129.45, 129.70, 144,30, 146.38(12× Ar—C), 178,64(-C=O)

4. MS: 358(M$^+$)
5. IR: Cm$^{-1}$ 3560(-OH), 1765 (γ-lactone)
6. $[\alpha]_D$: -37.09 (28° C.)

(-)-Wikstromol

1. Molecular formula: $C_{20}H_{22}O_7$
2. $^1$H-NMR : 2.40–2.55(2H, m), 2.65–2.80 (2H, m), 3.10–3.20(1H, d), 3.85(6H, d), 3.95(2H,br d) 5.60(2H, d), 6.50–6.80(6H, m)
3. $^{13}$C-NMR: δ 31.50(C-7), 41.90(C-8), 43.74(C-7), 55.94(2×—OMe), 70.26(O—CH$_2$—O,) 76.33(—C—OH) 111.55, 112.81, 114.35, 114.56, 116.82, 121.42, 123.12, 126.20, 130.35, 144.27, 144.95, 146.59(12× Ar—C)
4. MS: 374(M$^+$)
5. $[\alpha]_D$: -30.90 (28° C.)

EXAMPLE -2

Figure 1A:
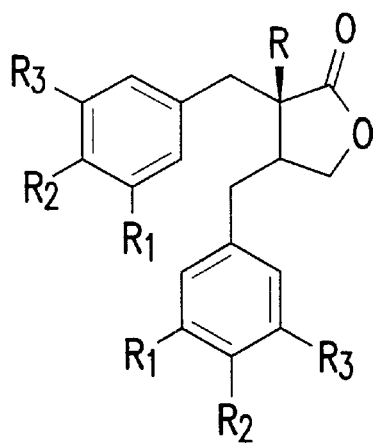
FIG. 1(*a*): represents hydroxyl substituted 3, 3$^1$-dimethoxylignan-9, 9$^1$-olide.
Figure 1B:
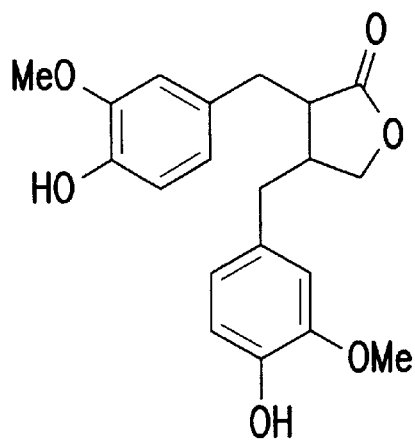
Figure 1C:
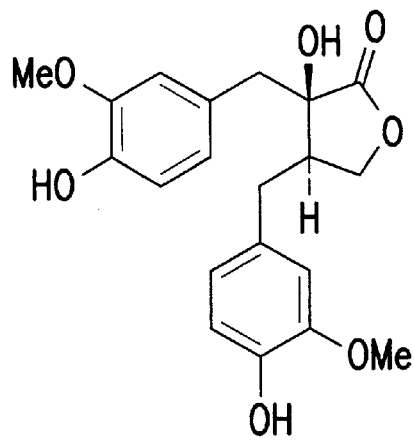
Figure 2A:
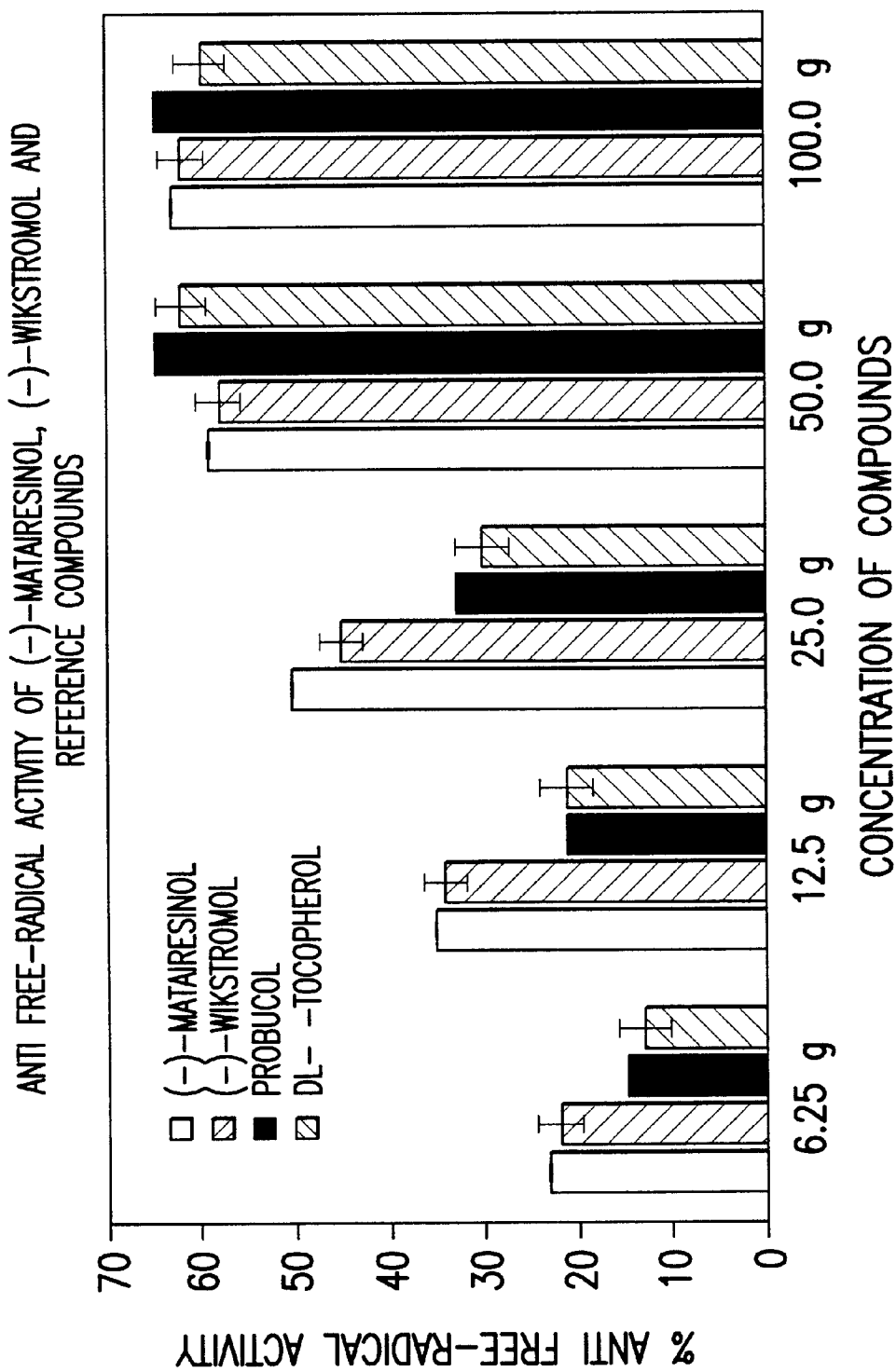
FIGS. 2(*a*)&(*b*): are graphical representations depicting free-radical activity of (−)-Matairesinol and (−)-wikstromol.
Figure 2B:
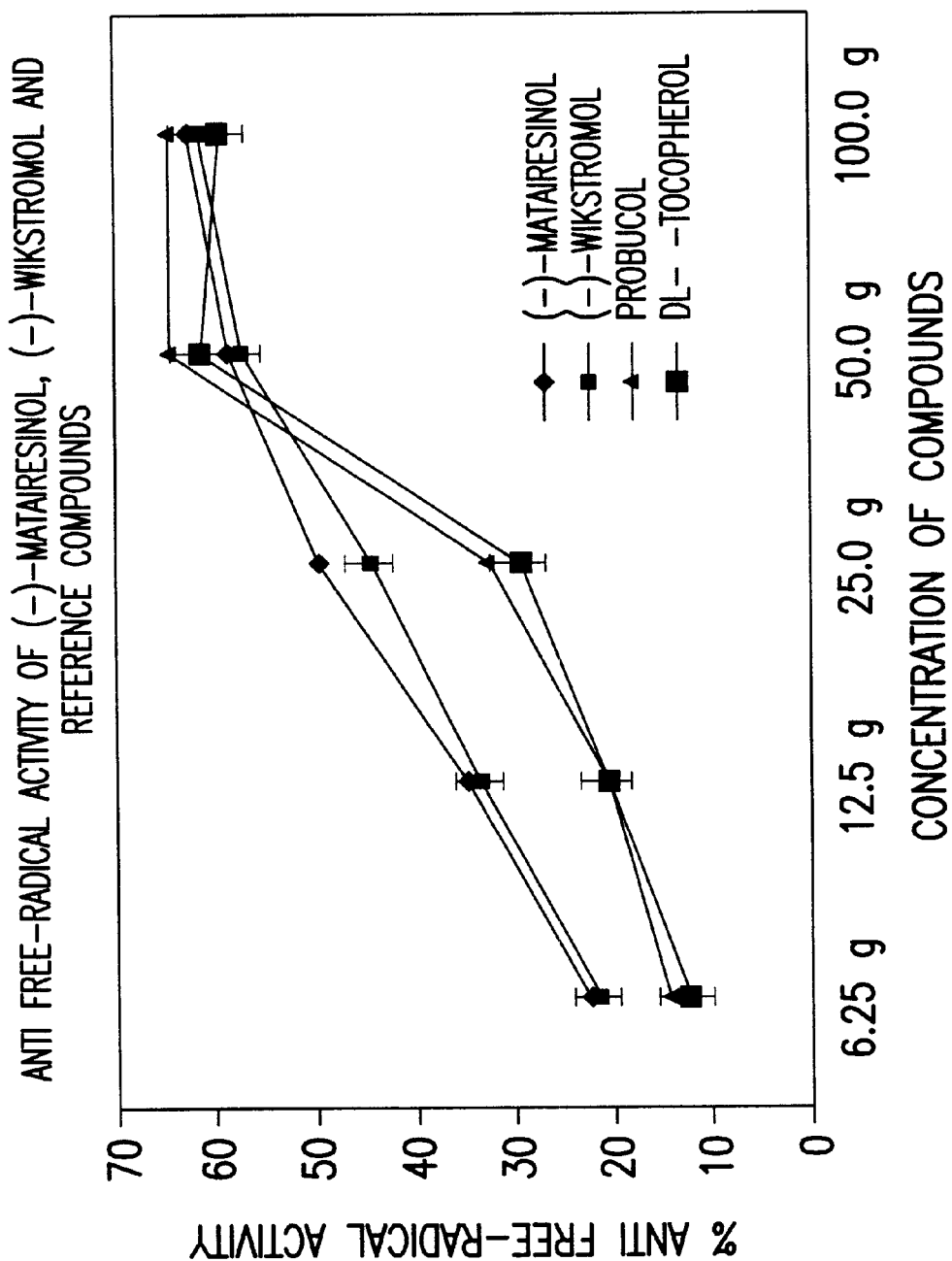

In vitro evaluation of free radical scavenging antioxidant potency:

Antioxidant activity of the compounds ((-)-Matairesinol and (-)-wikstromol) were tested for their capacity/potency to scavenger most widely used free radical 2,2-diphenyl-1-picryl hydroxyl radical (DPPH). The well-accepted and tested probucol and α-tocopherol were taken as reference compounds. 1 mg/ml DMSO concentration of the compounds [(-)-Matairesinol and (-)-wikstromol] were prepared and subsequently, serially diluted to lower concentrations with DMSO 100 ml of test compounds were reconstituted to 1 ml in Tris-HCl buffer (pH 7.4) equal volume of 500 μm of DPPH radical dissolved in ethanol was reacted with this. After incubation for 45 minutes in dark, the absorbency at 517 nm was recorded. Radical with no compound was taken as control for calculation of % radical scavenging activity. All the readings were recorded in triplicate. Results (FIGS. 2(a)&(b)) show that compounds under consideration possess more potent antioxidant/radical scavenging potency than reference standards. FIGS. 2(a)&(b) shows the data wherein the antioxidant activity of (-)-Matairesinol and (-)-wikstromol in comparison to commonly used Producol and Vitamin-E. It is well observed that the test compounds consistently show higher antioxidant activity than reference compounds in much lower concentrations.

In accordance with the practice of this invention, it has been found that (-)-matairesinol and (-)-wikstromol are isolated from a new source *Cedrus deodara* in significant yields. Also, it has been found that (-)-matairesinol and (-)-wikstromol show antioxidant properties.

ADVANTAGES

Antioxidant compounds recently have attracted the attention due to their broad spectrum activities in disorders of multiple origin viz., coronary heart disease, cancer, diabetes, rheumatic disorders and inflammatory condition where free radicals in causing/fostering the disease play important role. Much attention is being directed now to harness and harvest the antioxidant compounds from natural resources.

The compounds (-)-Matairesinol and (-)-wikstromol are used in pure form.

Hence, the usage is more advantageous than a mixture of compounds having similar properties, which are in current use. It is also important to note that the process of isolation of (-)-Matairesinol and (-)-wikstromol is highly economical when compared to the isolation of tocopherol which is a widely used antioxidant.

(-)-Matairesinol and (-)-wikstromol are used at a high degree of purity of over 90%. They are found to be highly effective when administered at a dosage of 250 mg/kg of body weight.

What is claimed is:

1. A method of treating arteriosclerosis, comprising the step of:
    administering an effective amount to a patient of a composition, comprising an active principal comprising (-)-wikstromol and/or (-)-matairesinol together with or in combination with therapeutically acceptable additives.

2. The method according to claim 1, wherein the additive is one or more carbohydrates, one or more proteins, or a mixture thereof.

3. The method according to claim 1, wherein, the ratio of the additive to the active principal ranges between 0.4:10 to 2:10.

4. The method according to claim 1, wherein, (-)-wikstromol and/or (-)-matairesinol is administered in the range of 250 to 300 mg per dose, twice a day.

5. The method according to claim 1, wherein, (-)-wikstromol and/or (-)-matairesinol is administered orally.

* * * * *